United States Patent [19]

Okada et al.

[11] Patent Number: 5,107,131
[45] Date of Patent: Apr. 21, 1992

[54] METHOD AND APPARATUS FOR EDGE DETECTION OF TRANSPARENT FILMS

[75] Inventors: Hiromi Okada; Masuo Kabutomori, both of Fujinomiya; Hiroshi Ikeno; Tamio Saitou, both of Hachioji, all of Japan

[73] Assignees: Nireco Corporation; Fuji Photo Film Co., Ltd., both of Japan

[21] Appl. No.: 528,509

[22] Filed: May 25, 1990

[30] Foreign Application Priority Data

Jun. 2, 1989 [JP] Japan .................................. 1-141934

[51] Int. Cl.$^5$ ............................................. G01N 21/86
[52] U.S. Cl. ..................................... 250/560; 250/225
[58] Field of Search ............... 356/370, 346, 347, 376; 250/561, 560, 225

[56] References Cited

U.S. PATENT DOCUMENTS 2,904,700  9/1959  Rockey .............................. 250/225

Primary Examiner—David C. Nelms
Assistant Examiner—T. Davenport
Attorney, Agent, or Firm—Lowe, Price, LeBlanc & Becker

[57] ABSTRACT

A method for detection of the edge and/or shape of transparent films, wherein the incident rays from a light source enter a polarizer to yield the linearly polarized light for irradiation to a transparent film with a property of rotatory polarization, and the rotatorily polarized light therefrom is transmitted through an analyzer with a polarization axis orthogonal to that of the polarizer, allowing the transmitted light to indicate the edge position and/or shape of the transparent film. An apparatus for detection of the edge and/or shape of transparent films, which is furnished with a polarizer, analyzer and detector to utilize the property of rotatory polarization of a transparent film placed between the polarizer and the analyzer, wherein the polarizer linearly polarizes the incident rays from a light source, emitting the light to be fed to the analyzer, a polarization axis of which is orthogonal to that of the polarizer, and the detector recognizes the output of the analyzer.

7 Claims, 4 Drawing Sheets

METHOD AND APPARATUS FOR EDGE DETECTION OF TRANSPARENT FILMS

BACKGROUND OF THE INVENTION

This invention relates to a method and apparatus for the edge detection of transparent films, specifically, for detection by means of polarized light of position and shape of the edge of transparent films with the property of rotatory polarization.

The edge position of web like opaque films has been detected with photoelectric sensors in response to the interception by the web of irradiated rays on the area of the edge. For transparent webs the pneumatic devices have been employed, as described in the references (see, for example, "Functions of present-day sensors and their optimal exploitation," Gijutsu-Hyoron-sha, 1981, pp. 65-67). FIGS. 4A and 4B illustrate a mechanism in the devices. In FIG. 4A the device controls the movement of web edge at a desired position in winding or unwinding a web. The edge of web is placed inside of the sensing nozzle of U-shape, and the low-pressure air (200~400 mm H₂O) is injected to the lower side of the web, which interrupts the air flow to change the recovery pressure to the sensing nozzle. The extent of interruption is dependent on the edge position of web so that the relationship of the displacement of the edge with the recovery pressure is as shown in FIG. 4B. The change in recovery pressure is transformed through the diaphragm into the displacement of the spool, which controls the hydraulic cylinder.

The optical methods like photoelectric sensors cannot be applied to detection of the edge of transparent films. The pneumatic methods, however, are less satisfactory than the optical methods with respect to accuracy and response in detection. The pneumatic devices also require clean air as well as ever clean environment to keep the ambient dust from suction.

SUMMARY OF THE INVENTION

It is accordingly an object of this invention to provide a method and apparatus for detection of the edge of transparent films.

This invention has as another object the provision of a method and apparatus for detection of the two-dimensional shape of transparent films.

This invention accomplishes the objects with the method and apparatus that detects the edge of transparent films by sensing the transmission through the analyzer of linearly polarized light rotated by the transparent film placed between the polarizer, which linearly polarizes the incident rays, and the analyzer, which transmits only the linearly polarized light orthogonal to the linearly polarized light emitted from the polarizer.

DESCRIPTION OF THE PREFERRED EMBODIMENT

Some preferred embodiments of the invention will be described hereinbelow on reference to the accompanying drawings.

Figure 1:
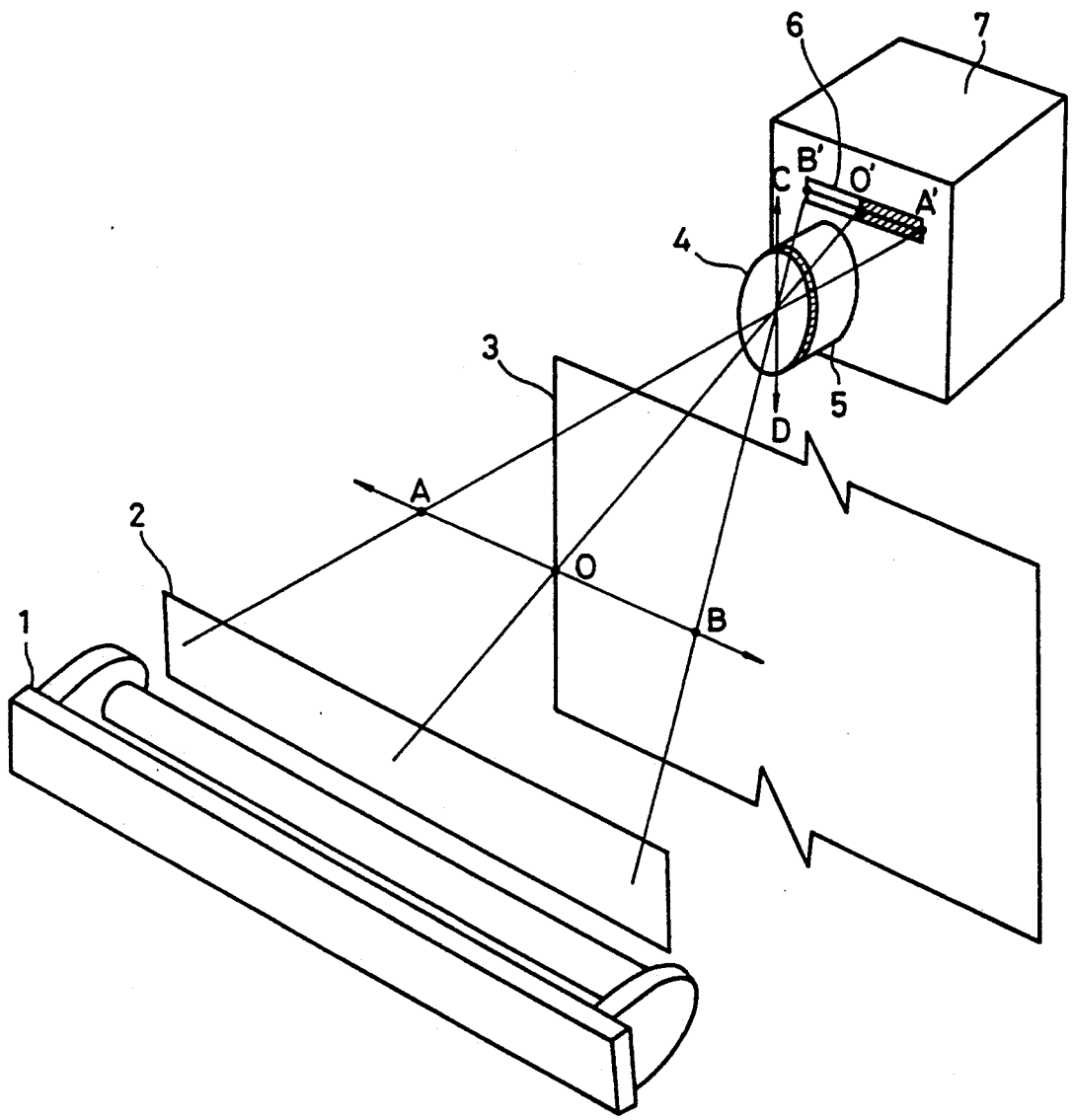
FIG. 1 is a general illustration of structure showing the first embodiment of the present invention of apparatus for detection of the edge of transparent films.

On reference to FIG. 1 the light source 1 is finished by a fluorescent lamp to supply a sufficient and uniform illumination for the whole range of position to be detected. The polarization film 2 on the side of the light source 1 is a polarizer of enough size to irradiate the linearly polarized light on the whole range of edge position of the objective transparent film 3 that has a property of rotatory polarization. The polarization filter 4 on the side of the camera is an analyzer, which is so placed as to transmit only the linearly polarized light orthogonal to the linearly polarized light from the polarization filter 2 on the side of the light source 1. The light transmitted through the polarization filter 4 on the side of the camera forms an image by the lens 5 on the one-dimensional image sensor 6, which works as the photo-receptive elements to transform the image formed by the lens 5 into the electric signals. The one-dimensional image sensor 6 comprises solid-state image pick-up elements or image pick-up tubes. The camera 7 is composed of the polarization filter 4, the lens 5 and the one-dimensional image sensor 6.

The manner of operation of the above described apparatus will be explained in the following.

Figure 2:
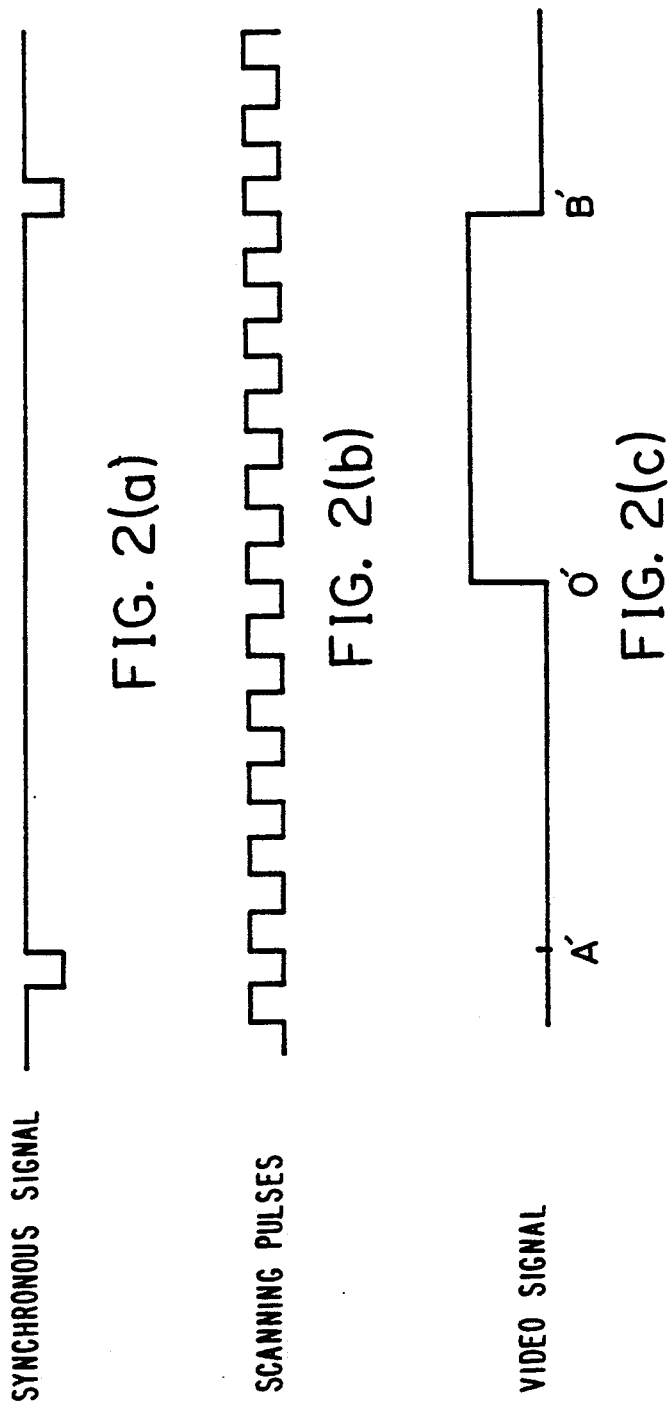
FIG. 2A is a diagram containing the wave form of a synchronous signal.
FIG. 2B is a diagram containing the wave form of scanning pulses.
FIG. 2C is a diagram containing the wave form of a video output signal from the image sensor.

The light source 1 emanates the incident rays to the polarization filter 2 on the side of light source, through which the linearly polarized light with the plane of polarization in the direction AB in FIG. 1 emits. A part of the linearly polarized light transmit through the transparent film 3, undergoing the rotatory polarization due to the property of the film. The polarization filter 4 on the side of camera is arranged to have the plane of polarization in the direction CD, which is orthogonal to the direction AB. The linearly polarized light emitted from the polarization filter 2 on the side of light source and fed directly to the polarization filter 4 on the side of camera cannot transmit through the polarization filter 4 because of its plane of polarization in the direction AB. On the other hand, the linearly polarized light rotated by transmission through the transparent film 3 has a component in the direction CD, which can transmit through the polarization filter 4 on the side of camera. The image formation by the lens 5 thus yields a dark image A'O' for a line element AO and a bright image O'B' for a line element OB after transmission through the transparent film 3. These dark and bright images are formed on the photo-receptive surface of the one-dimensional image sensor 6 and scanned in the direction from A' to B' in FIG. 1 to detect the edge position of the transparent film 3. The process of detection is explained by reference to FIGS. 2A-2C. The signal (a) in FIG. 2A is the synchronous signal with a frequency of horizontal scanning period from the terminal element on one end to the terminal element on the other end of the image sensor 6. The signal (b) in FIG. 2B is the scanning pulses for every element. The signal (c) in FIG. 2C is the video signal from every element, in which the positions of A',B', and O' correspond to the positions of A',B', and O' in FIG. 1, respectively, to form the bright image O'B' and the dark image O'A' with a stepwise change at the position O' of the edge of the transparent film 3. The video signal can be used for measurement of, for instance, the distance between A and O in FIG. 1 by counting the scanning pulse number in FIG. 2B between A' and O' in FIG. 2C, multiplied with the resolution power, i.e., ratio of the pitch of elements in the one-dimensional image sensor 6 to the magnification of the lens 5. The position of the edge thus can be determined for the transparent film 3, In this first embodiment the contrast more than 5 times is attained for the images with and without a polyester film of 0.15 mm thickness. The change in the path line of film does not affect the measurement. With incident rays vertical to the film the tilt angle of ±8° has no effect on the accuracy of measurement.

Figure 3:
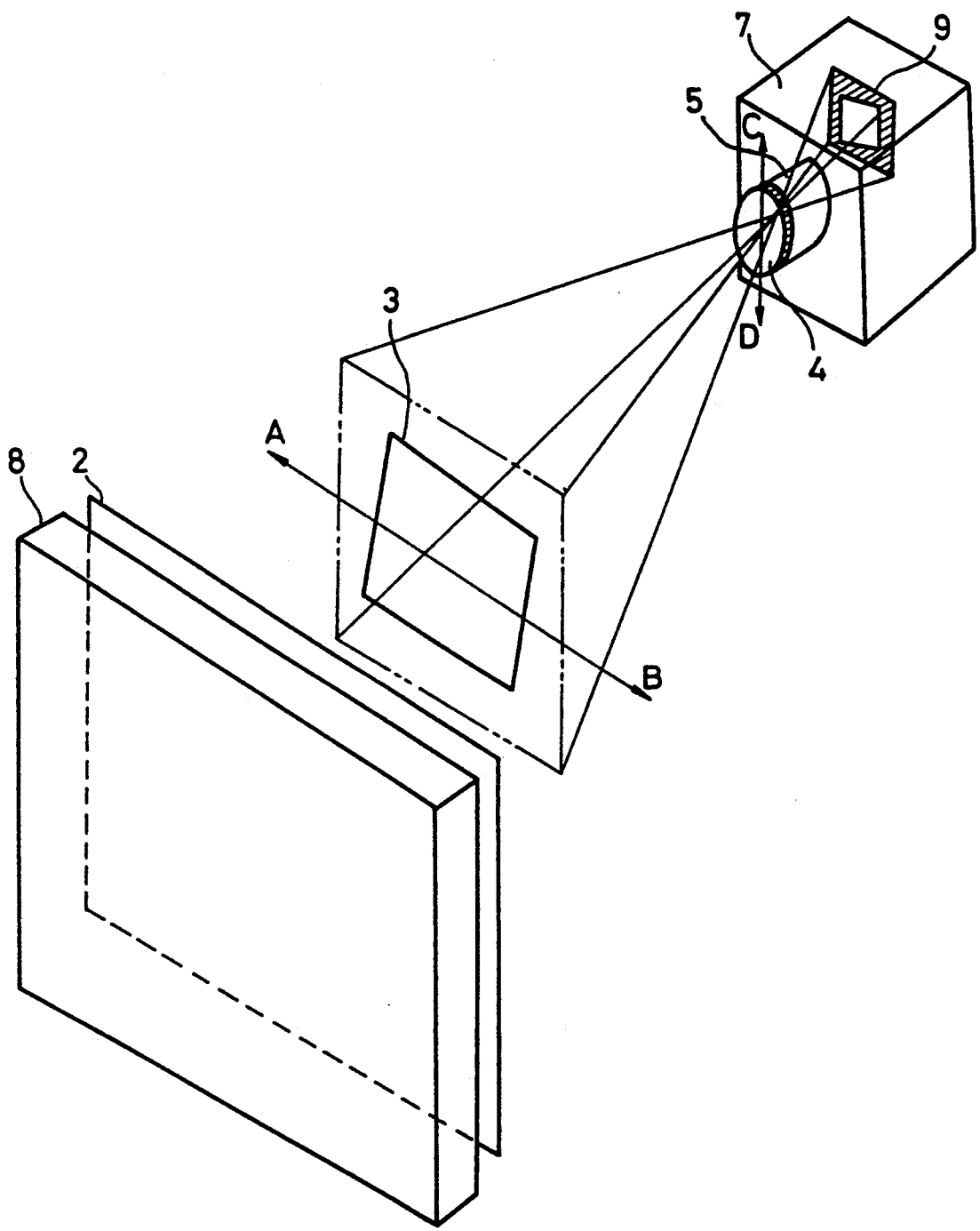
FIG. 3 is a general illustration of structure for the second embodiment of the present invention of apparatus for detection of the edge of transparent films.
Figure 4A:
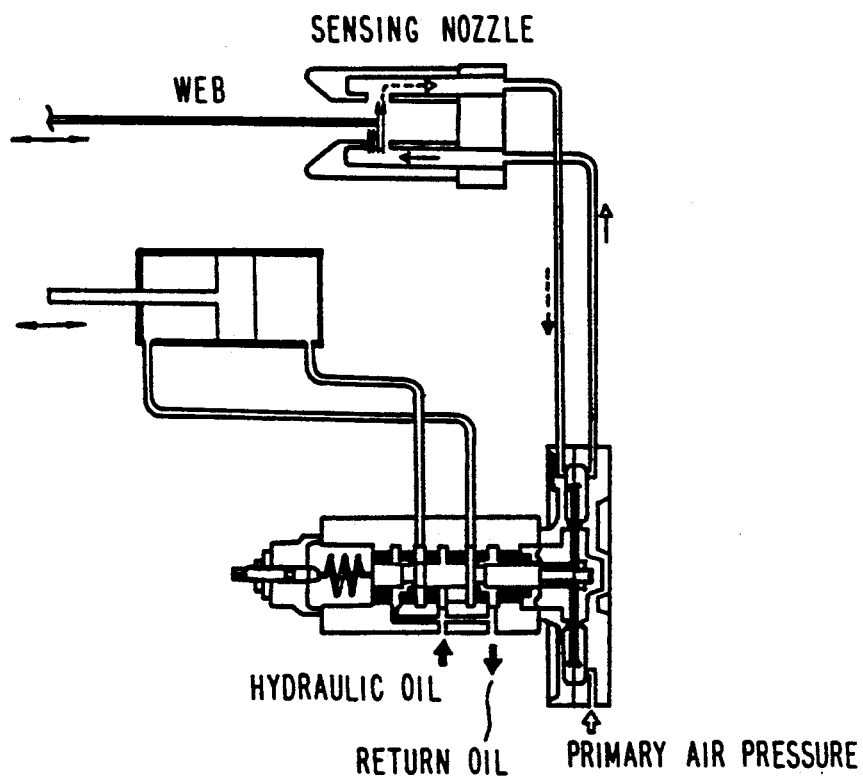
FIG. 4A illustrates a general structure of pneumatic control device for the position of web edge.
Figure 4B:
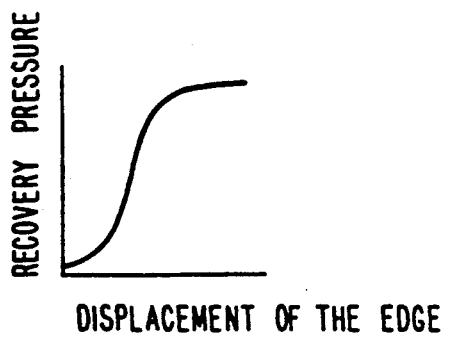
FIG. 4B shows the relationship between the displacement of web and the recovery pressure in the device of FIG. 4A.

The second embodiment is now described by reference to FIG. 3, which provides the measurement of shape, size and angle of the transparent film 3. In FIG. 3 the same symbols used in FIG. 1 indicate the same meanings. The areal light source 8 is made of, for example, several fluorescent lamps and a spreading plate. The two-dimensional image sensor 9, which employs solid-state image pick-up elements or image pick-up tubes, has the arrangement of the photo-receptive surface located at the image forming plane of the lens 5.

The manner of operation of the above described apparatus will be explained in the following.

The areal light source 8 emanates the incident rays to the polarization filter 2 on the source side, through which the linearly polarized light with the plane of polarization in the direction AB emits. A part of the linearly polarized light transmit through the transparent film 3 to rotate the plane of polarization due to the property of rotatory polarization of the film. The residual part of the linearly polarized light and the light transmitted through the transparent film 3 enter the polarization filter 4 on the camera side, which has the plane of polarization orthogonal to that of the polarization filter 2 on the source side. Only the component with the plane of polarization in the direction CD of the linearly polarized light rotated by the transparent film 3 can transmit through the filter 4 to enter the lens 5 to form an image of the shape of the transparent film 3 on the two-dimensional image sensor 9. The analysis of the image by the method described on the reference to FIGS. 2A-2C leads to the measurement of shape, size, angle of rotation and others of the transparent film 3.

The two embodiments above described indicate the feasibility of detection and measurement of the edge position of transparent films in high accuracy and speed, that have been impossible or difficult with the conventional pneumatic and photoelectric sensors. Moreover, the detection (measurement) range of these conventional sensors is narrow (normally 5~10 mm), causing the relocation of sensors for the web width exceeding the range. In the above embodiments location of a camera with the visual field of 1,000 mm at a fixed position about each edge of web makes it possible to measure the central position of web if its width varies between 1,000 mm and 3,000 mm. This method is applicable for sensors in the control devices of the edge position of moving transparent films as well as the measuring devices of shape, size, angle and others of a sheet of stationary transparent films.

It is also possible to use CdS or SPD as photo-receptive elements in analogue measurement, instead of image sensors, for the two embodiments above described. This method, however, is liable to cause more errors owing to direct responses of the elements to the disturbances in light source and path line as well as ambient light.

The explanation given hereabove clearly indicates that this invention provides a method for accurate measurement of the edge position, shape, size, angle and others of transparent films by utilizing the property of rotatory polarization of films.

Although some obvious changes may be made in the specific embodiment of the invention described herein, such modifications are within the spirit and scope of the invention claimed, implying that all materials contained herein are intended as illustrative and not as limiting in scope.

What is claimed is:

1. A method for detecting size, shape and incident angle of transparent films comprising the steps of:
   (a) linearly polarizing incident rays from a light source by a polarizer;
   (b) transmitting a part of said linearly polarized light through a transparent film with a property of rotatory polarization, and irradiating the transmitted light therefrom and the residual part of said linearly polarized light onto an analyzer, which transmits only linearly polarized light having a plane of polarization orthogonal to that of said linearly polarized light emitted from said polarizer; and
   (c) scanning an imager to detect edges of said transparent film by means of the transmitted light through said analyzer.

2. An apparatus for detection of the edge of transparent films comprising:
   (a) a polarizer of incident rays from a light source to emit the linearly polarized light;
   (b) an analyzer receiving directly a part of the linearly polarized light emitted from said polarizer and the residual part thereof after their transmission through a transparent film with a property of rotatory polarization, and transmitting only the linearly polarized light having a plane of polarization orthogonal to that of said linearly polarized light emitted from said polarizer; and
   (c) an array of photo-receptive elements for receiving the light transmitted through said analyzer to generate the image output signals.

3. An apparatus for detection of the edge of transparent films according to claim 2, wherein said array of photo-receptive elements is one-dimensional.

4. An apparatus for detection of the edge of transparent films according to claim 3, wherein said array of photo-receptive elements comprises a one-dimensional image sensor.

5. An apparatus for detection of the edge of transparent films according to claim 2, wherein said array of photo-receptive elements is two-dimensional.

6. An apparatus for detection of the edge of transparent films according to claim 5, wherein said array of photo-receptive elements comprises an imager.

7. The method of claim 1 further comprising the step of:
   (d) counting pulses of said imager and comparing pulse magnitudes to determine location of the edges of said transparent film.

* * * * *